(12) United States Patent
Selvaraj (10) Patent No.: US 10,959,681 B2
(45) Date of Patent: Mar. 30, 2021

(54) NONINVASIVE BLOOD PRESSURE MEASUREMENT AND MONITORING

(71) Applicant: Vital Connect, Inc., San Jose, CA (US)

(72) Inventor: Nandakumar Selvaraj, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 303 days.

(21) Appl. No.: 15/491,413

(22) Filed: Apr. 19, 2017

(65) Prior Publication Data
US 2018/0303434 A1 Oct. 25, 2018

(51) Int. Cl.
| A61B 5/00 | (2006.01) |
| A61B 7/04 | (2006.01) |
| A61B 5/021 | (2006.01) |
| A61B 5/318 | (2021.01) |
| A61B 5/349 | (2021.01) |

(Continued)

(52) U.S. Cl.
CPC ............ *A61B 5/7278* (2013.01); *A61B 5/021* (2013.01); *A61B 5/02125* (2013.01); *A61B 5/02416* (2013.01); *A61B 5/318* (2021.01); *A61B 5/349* (2021.01); *A61B 5/6801* (2013.01); *A61B 7/00* (2013.01); *A61B 7/045* (2013.01); *A61B 5/6833* (2013.01); *A61B 5/7203* (2013.01); *A61B 5/7239* (2013.01); *A61B 5/7267* (2013.01); *A61B 2562/028* (2013.01); *A61B 2562/0219* (2013.01)

(58) Field of Classification Search
CPC . A61B 5/02416; A61B 5/021; A61B 5/02125; A61B 5/0205; A61B 5/0402; A61B 5/6833; A61B 5/0404; A61B 5/0006; A61B 5/0245; A61B 5/742; A61B 5/746

USPC .......................... 600/300, 310, 324, 483–485
See application file for complete search history.

(56) References Cited

U.S. PATENT DOCUMENTS

| 8,235,910 B2 * | 8/2012 | Parlikar | ................ A61B 5/021 600/485 |
| 8,442,607 B2 * | 5/2013 | Banet | ................ A61B 5/02055 600/324 |
| 10,136,827 B2 * | 11/2018 | Banet | ................ A61B 5/02055 |

(Continued)

FOREIGN PATENT DOCUMENTS

| WO | 2015/073909 A1 | 5/2015 |
| WO | 2016/155138 A1 | 10/2016 |

OTHER PUBLICATIONS

Extended European Search Report from EP Application No. EP18787298.1 dated Dec. 14, 2020, 9 pages.

(Continued)

*Primary Examiner* — May A Abouelela
(74) *Attorney, Agent, or Firm* — Brundidge & Stanger, P.C.

(57) ABSTRACT

A Noninvasive Blood Pressure (NIBP) device, method, and system may employ one or more sensors configured to sense physiological changes associated with cardiovascular function and provide signals corresponding to the sensed physiological changes; one or more signal detectors to detect an ECG signal, a PPG signal, and a PCG signal from the signals provided by the one or more sensors; a computational system configured to derive signal features related to the detected signal waveforms; process the signal features to determine measurements of noninvasive blood pressure using one or more independent prediction models; and output a result of the determination.

20 Claims, 10 Drawing Sheets

(51) Int. Cl.
*A61B 5/024* (2006.01)
*A61B 7/00* (2006.01)

(56) References Cited

U.S. PATENT DOCUMENTS

| | | | | |
|---|---|---|---|---|
| 2008/0077026 A1* | 3/2008 | Banet | A61B 5/02055 | 600/509 |
| 2008/0082004 A1* | 4/2008 | Banet | A61B 5/02028 | 600/485 |
| 2012/0330126 A1* | 12/2012 | Hoppe | A61B 5/0002 | 600/391 |
| 2013/0041268 A1* | 2/2013 | Rimoldi | A61B 5/0295 | 600/479 |
| 2013/0060098 A1* | 3/2013 | Thomsen | A61B 5/02028 | 600/301 |
| 2014/0066782 A1* | 3/2014 | Addison | A61B 5/024 | 600/476 |
| 2014/0081152 A1* | 3/2014 | Clinton | A61B 5/7235 | 600/479 |
| 2014/0275867 A1* | 9/2014 | Meehan | A61B 5/14552 | 600/310 |
| 2015/0057554 A1* | 2/2015 | Watson | A61B 5/02125 | 600/485 |
| 2015/0250422 A1* | 9/2015 | Bay | A61B 5/6833 | 600/391 |
| 2016/0066801 A1* | 3/2016 | Kahlert | A61B 5/0053 | 600/484 |
| 2016/0081563 A1* | 3/2016 | Wiard | A61B 5/0285 | 600/485 |
| 2016/0143546 A1* | 5/2016 | McCombie | A61B 5/026 | 600/480 |
| 2016/0143597 A1* | 5/2016 | Chang | A61B 5/0205 | 600/301 |
| 2016/0220122 A1* | 8/2016 | Luna | A61B 5/0452 | |
| 2017/0065191 A1* | 3/2017 | Jayaraman | A61B 5/021 | |
| 2017/0079533 A1* | 3/2017 | Robinson | A61B 5/02007 | |
| 2017/0209053 A1* | 7/2017 | Pantelopoulos | A61B 5/02125 | |
| 2017/0340209 A1* | 11/2017 | Klaassen | A61B 5/021 | |
| 2017/0347894 A1* | 12/2017 | Bhushan | A61B 5/0205 | |
| 2018/0085011 A1* | 3/2018 | Ma | A61B 5/7203 | |
| 2018/0108440 A1* | 4/2018 | Stevens | G16H 40/67 | |
| 2018/0228444 A1* | 8/2018 | Banerjee | G06N 20/00 | |
| 2018/0360315 A1* | 12/2018 | Fujita | A61B 5/0024 | |
| 2019/0167105 A1* | 6/2019 | Shrubsole | G16H 10/60 | |

OTHER PUBLICATIONS

Kachuee Mohammad, et al., "Cuffless Blood Pressure Estimation Algorithms for Continuous Health-Care Monitoring", IEE Transactions on Biomedical Engineering, IEEE Service Center, vol. 64, No. 4, Apr. 1, 2017, pp. 859-869, XP011642867.

Enric Monte-Moreno, "Non-Invasive Estimate of Blood Glucose and Blood Pressure from a Photoplethysmograph by Means of Machine Learning Techniques", Artificial Intelligence in Medicine, vol. 53, No. 2, Oct. 1, 2011, pp. 127-138, XP055013563.

* cited by examiner

NONINVASIVE BLOOD PRESSURE MEASUREMENT AND MONITORING

TECHNICAL FIELD

The present disclosure relates to measuring and monitoring of noninvasive blood pressure, and more particularly, to a sensor device including wearable, wired and/or wireless features, that is utilized to measure noninvasive blood pressure in a clinical monitoring environment.

BACKGROUND

The field of noninvasive blood pressure (NIBP) monitoring and measurement continues to draw research interest, some centering on pneumatic cuff-based methods including oscillometry. Numerous studies have validated the clinical utility of monitoring vascular unloading (using the volume-clamp principle) in various subject groups, but questions of consistency in certain conditions, including hypotension or vascular insufficiency, reliability in absolute magnitude, sensor attachment issues, and undesirably frequent recalibration routines have been raised. For these and other reasons, cuff-based oscillometry may be an imperfect solution for NIBP in general, and long-term NIBP in particular.

Development of medical devices for NIBP is evolving, including optical sensor mounting at finger/wrist and ear-lobe/forehead locations. Monitoring and measurement of NIBP at these locations may use pulse transit time (PTT) as a measurement of the rate of pulse wave propagation through the vascular system.

In some examples, PTT may be calculated on the basis of the difference between pulse arrival time (PAT) and pre-ejection period (PEP). The correlation of PTT or PAT to blood pressure (BP) in pharmacological and physiological interventions may be considered uncertain, and unreliable for predicting beat-to-beat NIBP for medical applications. Therefore, a convenient approach to reliable NIBP monitoring and measurement using a sensor device is needed.

SUMMARY

A method and system for determining and monitoring measurements of noninvasive blood pressure are disclosed.

In a first aspect, a sensor device comprises one or more sensors configured to sense physiological changes associated with cardiovascular function and provide outputs corresponding to the sensed physiological changes; one or more signal detectors to detect an ECG (electrocardiograph) signal, a PPG (photoplethysmograph) signal, and a PCG (phonocardiograph) signal from the outputs provided by the one or more sensors; and a computational system configured to: derive signal features including cardiac timing intervals from the detected ECG, PPG, and PCG signals; process the signal features to determine measurements of NIBP using one or more independent prediction models; and output a result of the determination.

In a second aspect, a method to predict noninvasive blood pressure comprises sensing physiological changes associated with cardiovascular function; detecting ECG, PPG, and PCG signals based on the sensed physiological changes; deriving signal features including cardiac timing intervals from the detected ECG, PPG, and PCG signals; processing the signal features; determining measurements of NIBP from the processed signal features using one or more independent prediction models; and outputting a result of the determination.

In a third aspect, system to predict NIBP comprises a sensor device including: one or more sensors configured to sense physiological changes associated with cardiovascular function and provide outputs corresponding to the sensed physiological changes; one or more signal detectors to detect an ECG signal, a PPG signal, and a PCG signal from the outputs provided by the one or more sensors; a processor to derive signal features including cardiac timing intervals from the ECG signal, PPG signal, and PCG signal; and a wireless transmitter configured to transmit wirelessly the extracted signal features; and a computational system configured to: process the signal features to determine measurements of NIBP using one or more independent prediction models; and output a result of the determination.

DETAILED DESCRIPTION

The present disclosure relates to noninvasive blood pressure measurement or monitoring and, more particularly, to a device, system, and method to determine NIBP using a plurality of physiological changes associated with cardiovascular function measured by a sensor device. Examples of the sensor device include, but are not limited to, wearable sensor devices, wired or wireless sensor devices, and sensor devices that may incorporate both wired and wireless features. In one or more embodiments, wired and/or wireless sensor devices may be wearable, in whole or in part.

The following description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

High BP is a risk factor for many cardiovascular and renal diseases. By some estimates, one third of adults in the US have either hypertension (a health condition having systolic blood pressure (SBP)≥140 mmHg and a diastolic blood pressure (DBP)≥90 mmHg) or are taking anti-hypertensive medications. Another one-quarter of US adults have prehypertension with SBP between 120-139 mmHg and DBP between 80-89 mmHg, a condition in between the normal and hypertensive levels. Further, half of older US adults are living with hypertension. Treatment with anti-hypertensive medication has been shown to reduce the risk of cardiovascular events, such as heart failure or heart attack, myocardial infarction, sudden death, organ damage and stroke by way of nonlimiting example. Accurate BP measurement can help to identify and treat individuals with hypertension and reduce BP related morbidity and mortality.

As part of standard patient monitoring in clinical conditions, BP is a vital sign routinely measured using manual auscultatory technique, where an upper arm cuff is inflated and slowly deflated while a healthcare practitioner listens to phase I-V of Korotkoff sound over the brachial artery with a stethoscope. Though this inexpensive method is considered as a clinical standard for noninvasive intermittent monitoring, it relies on well-trained professionals and may be subject to human and cuff size errors.

An oscillometry technique is an alternative automatic noninvasive method used in clinical practice, where an upper arm cuff is inflated and slowly deflated while the presence of oscillations are detected electronically via the cuff using a pressure sensor located inside the cuff, thereby determining the MBP as the cuff pressure that produces a maximal amplitude of oscillations. The oscillometry technique may indirectly estimate SBP and DBP based on measured maximal amplitude and empirical algorithms. For example, SBP and DBP values may be estimated as the cuff pressure that correspond to 0.5 and 0.66 of the maximal amplitude of oscillations, respectively. Even though this objective method is popular, convenient, and does not require a skilled operator, the choice of cuff size, proper application of cuff per human judgment, and manufacturer's algorithm are factors that determine the accuracy of measurement. In addition, the automated oscillometry device may not be suitable for continuous BP readings since the procedure may take at least 30 s to take one BP measurement, and it may not be suitable to measure rapid changes in BP.

Further, the accuracy of the manual auscultatory or automated oscillometry procedures in clinic for correctly diagnosing hypertension may be dubious due to the "white coat" effect, which is the tendency of BP to increase in the presence of a physician, as well as an inherent variability in BP over the course of a day. Compared to office BP measurement, day-by-day BP measurement at home and its variability may have more prognostic significance and be a more powerful indicator of target organ damage and cardiovascular risk.

Continuous measurement of BP variability at regular intervals may have a prognostic value for cardiovascular-related morbidity and mortality. Therefore, reliable continuous noninvasive blood pressure (NIBP) measurement would be valuable for diagnosis and prognosis of cardiovascular diseases in clinical monitoring. Vascular unloading (using a volume-clamp principle) is a continuous NIBP technique that utilizes a PPG sensor and a cuff around finger where the pressure is adjusted beat-to-beat in order to maintain the finger blood volume a constant. This technique may be limited in clinical practice due to its high cost, inaccuracy in certain patients, and undesirably frequent calibration routines requiring an upper arm cuff. Thus, the cuff-centered NIBP techniques including auscultatory, oscillometry, and vascular unloading methods may be regarded as occlusive, cumbersome, and uncomfortable to patients.

A photometric method based on measurement of PTT may be an alternative univariate solution for continuous nonocclusive NIBP prediction, since the PTT measurement is shown to correlate with changes in BP, vascular elasticity or compliance, and other hemodynamic perturbations. However, frequent calibration (hourly/daily) using an upper arm cuff is not feasible in clinical settings in order to transform PTT variability into absolute magnitude of BP. Further, the accuracy and reliability of PTT for NIBP assessment as a medical practice may be uncertain.

A method and system in accordance with the present invention may utilize, in one or more embodiments, a wireless, portable and wearable sensor device including a patch form factor applied on the user's (e.g., patient's) body, for example at or near a chest location, to automatically and/or continuously measure and/or quantify BP noninvasively.

In some aspects, the present invention may provide continuous measurements of NIBP without requiring a calibration procedure that, e.g., involves simultaneous measurement of single or multiple lead ECG signals, single or multiwavelength PPG signals, and/or PCG signals, and extraction of multivariate signal features including magnitudes and timing intervals within or between the detected physiological signals, and processes the multivariate signal features to determine absolute magnitudes of NIBP using one or more independent prediction models. According to one or more embodiments of the present invention, the determination of NIBP can be performed continuously and/or periodically over beats, minutes, hours, day-to-night, different body positions, ambulatory, or active conditions.

A wearable sensor may offer comfort and convenience for carrying out one or more physiological measurements and other bodily functions in the determination of NIBP described in detail herein.

Figure 1:
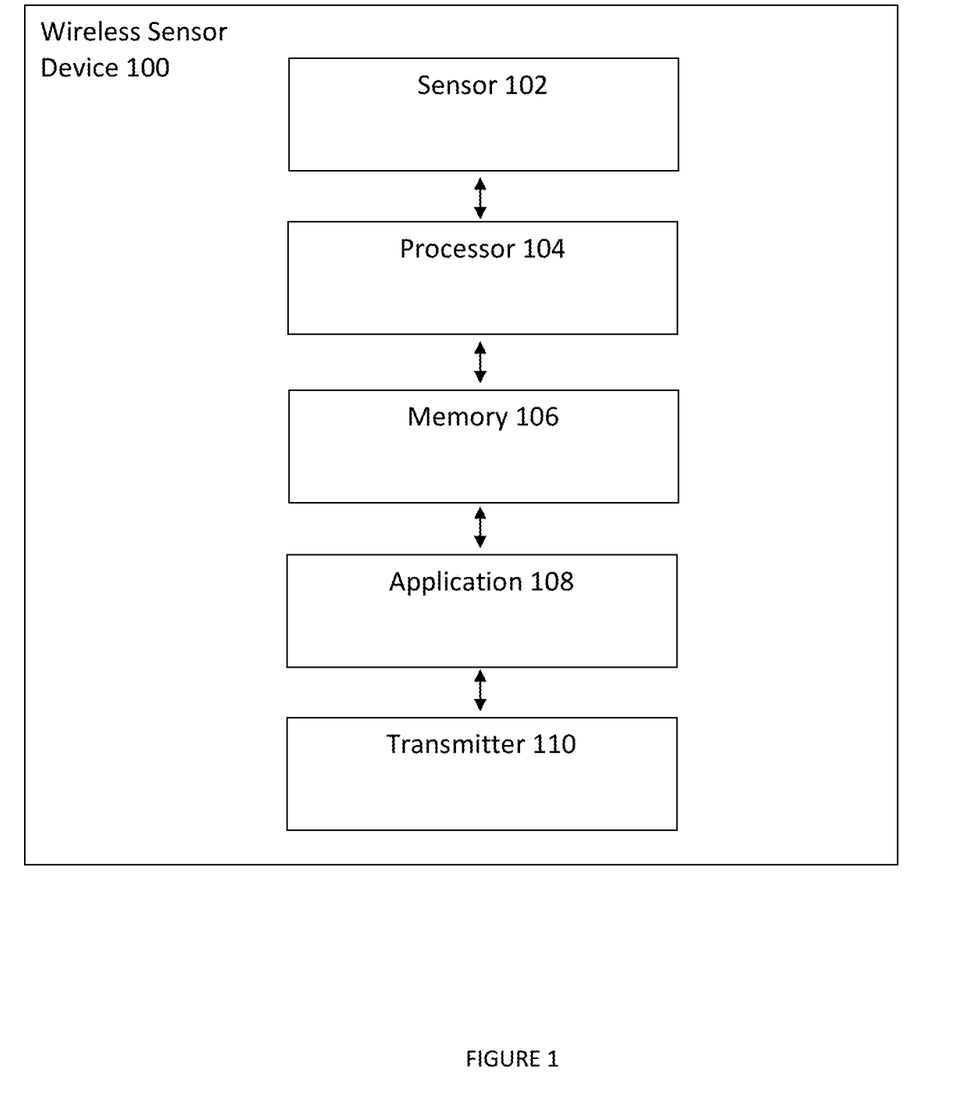
FIG. 1 illustrates features of one or more examples of a wireless sensor device for measurement of NIBP in accordance with one or more embodiments.

FIG. 1 illustrates features of one or more examples of a wireless sensor device 100 for measurement of NIBP in accordance with one or more embodiments. One or more features of the illustrated sensor device may also be applicable to partially wireless and/or wired sensor devices, and thus the wireless features of FIG. 1 should not be considered limiting of sensor device 100. Sensor device 100 may include a sensor 102, a processor 104 coupled to the sensor 102, a memory 106 coupled to the processor 104, an application 108 coupled to or stored in memory 106, and a transmitter 110 coupled to application 108. One of ordinary skill in the art readily recognizes that sensor device 100 can include other components and that the components of sensor device 100 can be coupled in a variety of different ways, and that such modifications would be within the spirit and scope of the present invention.

In one or more embodiments, sensor device 100 may be attached to a user to detect one or more physiological signals via sensor 102. Sensor 102 may sense physiological changes (e.g., in the form of or derivable from signals) from the user, which are transmitted to memory 106 and in turn available to application 108 for processing via processor 104. Processor 104 may execute application 108 to process and analyze the physiological signals to obtain signal features related to the user's BP. The information may be transmitted to transmitter 110 and in turn relayed to another user (e.g., doctor or technician or family member) or device for further processing, analysis, and/or storage. In one or more embodiments, transmitter 110 may transmit the various detected physiological signals in raw form to a remote device/server (e.g., smartphone, tablet, cloud-based server, etc.) for further processing, analysis, and/or storage.

In one or more embodiments, sensor 102 may be any of an embedded sensor with electrodes, a microelectromechanical system (MEMS) accelerometer, an optical system comprising light emitting diodes (LED) and photo-detector (PD), and processor 104 may be a microprocessor. One of ordinary skill in the art readily recognizes that a variety of devices can be utilized for sensor 102, processor 104, memory 106, application 108, and transmitter 110, and that such modifications or details would be within the spirit and scope of the present invention.

Additionally, one of ordinary skill in the art readily recognizes that a variety of wireless and/or wired sensor devices can be utilized including but not limited to wearable devices, a wireless and/or wired sensor device in a patch form-factor, electrocardiograph devices, tri-axial accelerometers, uni-axial accelerometers, bi-axial accelerometers, gyroscopes, pressure sensors and optical sensors, and that such modifications and details would be within the spirit and scope of the present invention.

In one or more embodiments, a wearable device may have an adhesive patch biosensor worn on the chest that incorporates, e.g., two surface electrodes with hydrogel on the bottom, a battery, an electronic module with an embedded processor or a system-on-chip and other electronic components and circuitry, a MEMS tri-axial accelerometer, optical sensor and a Bluetooth Low Energy (BLE) transceiver. The wearable device may be partly (semi-) disposable, disposable or reusable.

Figure 2:
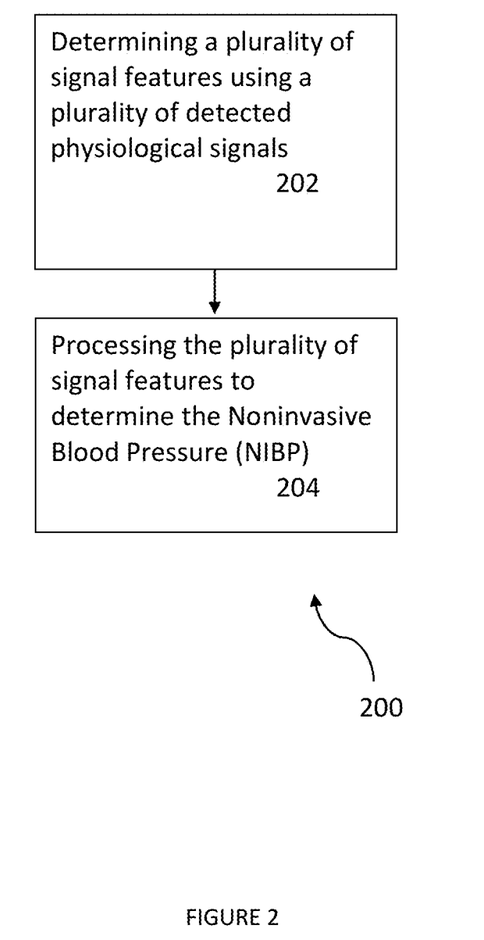
FIG. 2 illustrates an example of method features for determining BP noninvasively using a sensor device in accordance with one or more embodiments.

FIG. 2 illustrates an example of method features for determining BP noninvasively using a sensor device such as sensor device 100 in accordance with one or more embodiments. Method 200 may include determining a plurality of signal features of a plurality of physiological signals detected in a user (e.g., patient) in step 202, and processing the plurality of signal features to determine the noninvasive blood pressure (NIBP). In one or more embodiments, sensor device 100 may facilitate continuous and/or automated measurement and/or monitoring of a plurality of physiological signals including but not limited to single or multiple lead ECG signals, single or multiwavelength PPG signals, and/or PCG signals, and/or body acceleration signals.

In one or more embodiments, after sensor device 100 detects the plurality of physiological signals via a plurality of internal and/or embedded sensors, the processor of sensor device 100 may utilize a plurality of firmware algorithms to process one or more raw waveforms of the plurality of physiological signals and to transmit streams of the processed physiological variables via a BLE transceiver/link as encrypted data to a relay such as a smartphone. In some examples, the transmitted data may be live (real-time or near real-time) streams of data can be viewed and stored. The processing steps of method 200 may be performed by sensor device 100, an external device, a relay/cloud processor, a smartphone device, a tablet device, or a cloud computing system, or a combination of one or more of these.

Figure 3:
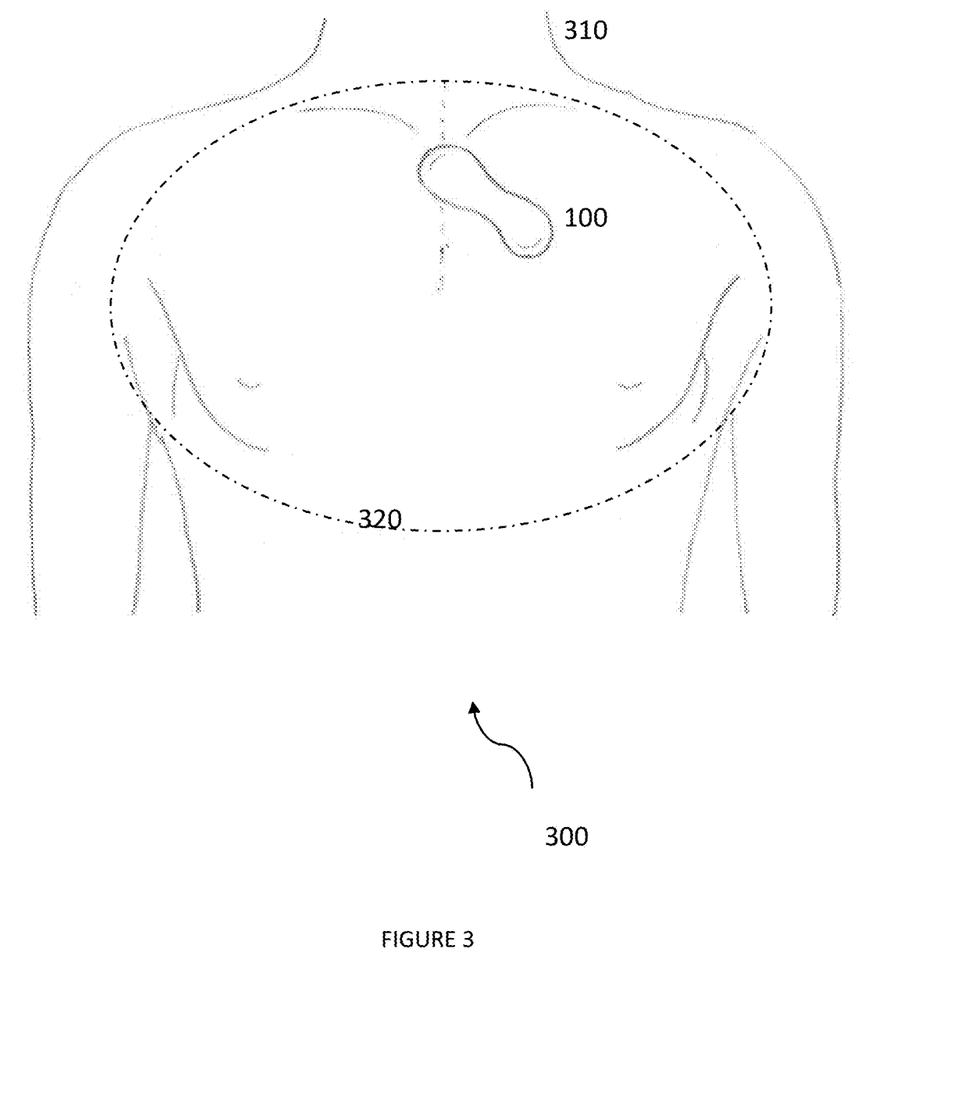
FIG. 3 illustrates a subject (e.g., patient) shown wearing an example of a wearable sensor device suitable for use in an NIBP wearable sensor system.

FIG. 3 illustrates a subject (e.g., patient) 310 shown wearing an example of a wearable sensor device 100 suitable for use in an NIBP wearable sensor system. Wearable sensor device 100 may be positioned at any location on the body suitable for its measuring and/or monitoring function or functions. For example, and without limitation, the location may be a region of the upper torso 320 (e.g., at or near the chest). A specific location suitable for monitoring certain conditions with one or more specific sensors or sensor form factors may include any of the locations and orientations such as left midclavicular line over intercostal space (ICS) 2 in a modified lead-II configuration, vertically over the upper sternum, and horizontally on the left midclavicular line over ICS 6. Wearable sensor device 100 may have sensors to monitor physiological characteristics or qualities related to subject 310. To this and other ends, wearable sensor device 100 may include hardware, firmware, and/or software to perform various sensing, processing, and transmitting of information related to the subject 310, as discussed more fully below.

Without limitation, wearable sensor device 100 may be a wireless and/or wired sensor device configured with one or more sensors to detect physiological characteristics and/or qualities of subject 310, a cover, a base, an output, and/or a display. The cover and base may be constructed, for example, of any material suitable to a wearable sensor device having at least the components and functions described herein. In one or more embodiments, wearable sensor device 100 may be attached to subject 310 via the base by, e.g., a skin-friendly adhesive or other device. In some embodiments, the base may be or comprise a wearable patch having an adhesive to attach the patch directly or indirectly to the subject's body. In this disclosure, wearable sensor device 100 may be referred to variously as a "wearable sensor device", "wearable sensor patch", or the like. A nonlimiting example of wearable sensor device 100 is a patch with any shape including but not limited to boomerang, oval, ellipse, rectangle, and triangle.

Wearable sensor device 100 may be configured to provide information via the output in the form of wireless and/or wired signals, a visible indicator, and/or an audible indicator, without limitation, and/or provide visible information via its display in addition to any of these.

Wearable sensor device 100 may have one or more sensors positioned to be in direct contact with subject 310 or separated from subject 310 by the base or other structure or device. Wearable sensor device 100 may have any number of sensors suitable for the functions described herein. Further, some or all of the sensors may be used in conjunction for various sensing objectives. In one or more embodiments, the sensors may include, without limitation, a PPG sensor comprising one or more light emitting diodes and photodiodes capable of measuring one or more wavelengths of optical signals, two or more ECG electrodes, and a PCG sensor comprising any of a MEMS, a piezoelectric film, piezoceramic disk and/or a microphone sensor.

Wearable sensor device 100 may include a battery and various electronic components, which may be configured to perform some or all of the processing and analysis described herein, and may be powered by the battery.

In general, wearable sensor device 100 may obtain any form of physiological, physical and demographical data from subject 310. (As herein used, "data" or "information" may be used in combination, singly, interchangeably, or in the alternative as context dictates or permits.) Such data may be processed by the electronic components, for example by a processor system-on-chip, to obtain various information by any combination of analog, digital, and/or algorithmic processes. (As herein used, "process" may include "analysis" with respect to data; these terms thus may be used in combination, singly, interchangeably, or in the alternative as context dictates or permits.) The obtained data may be stored in a memory on wearable sensor device 100, transmitted externally, or displayed, for example. According to at least one embodiment, the processor may execute instructions to process the data and obtain information regarding the subject, such as conditions related to the subject's health. Additionally or alternatively, the processed information may be transmitted externally to a user or device for any suitable purpose, such as information gathering, further processing, user or machine analysis, and/or storage. By way of non-limiting example, information such as physiological signals after analysis or in raw form may be transmitted to a remote device/server (e.g. a terrestrial or cloud-based server, or a mobile device such as a smartphone or tablet (not shown)). Information may be also or alternatively provided in audible or visible form, such as a verbal report or nonverbal signal (e.g., audible or visible alert).

One of ordinary skill in the art readily recognizes that a variety of sensors can be utilized, consistent with the data gathering, processing, and analysis described herein.

Figure 4:
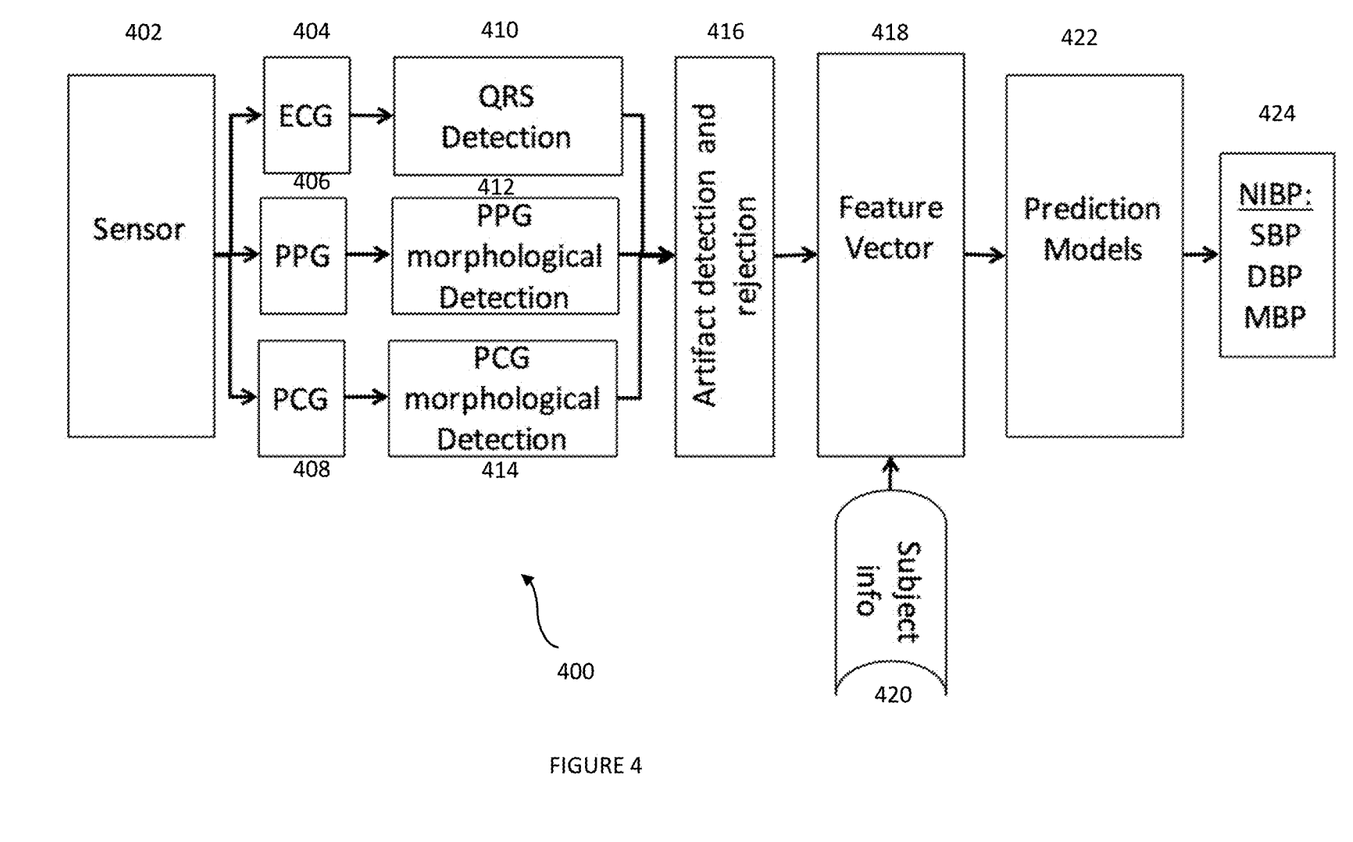
FIG. 4 illustrates a detailed flow chart of a method for determining NIBP of a user (patient) in accordance with one or more embodiments.

FIG. 4 illustrates a detailed flow chart of a method 400 for determining NIBP of a user (patient) in accordance with one or more embodiments. Sensor device 402, which may be wireless, wired, or have both wireless and wired features as described herein, may be embedded with electrodes, a MEMS accelerometer, an optical system comprising LEDs and/or a PD and, in accordance with one or more embodiments, may be attached on the body of a user at near the chest, for example. Sensor device 402 may sense one or more physiological changes (e.g., in the form of or derivable from signals) from the user, and process the raw signals by applying various signal processing steps including removal of power line noise and filtering to limit the signals with desired bandwidth, and produce continuous waveforms including, without limitation, one or more of ECG waveforms 404, PPG waveforms 406, and PCG waveforms 408. PCG waveforms used in this method can be high frequency band (audio) signals (for example >10 Hz) or an envelope of low-frequency signals derived from rectified or unrectified high frequency band signals.

In method 400, a suite of morphological detection algorithms may be utilized to detect various fiduciary points or events in ECG, PPG, and PCG signals. At block 410, a QRS wave of ECG signals may be detected to obtain the R wave peaks, in accordance with one or more embodiments, as a cardiac beat reference to determine various cardiac timing signal features. In addition or alternatively, a Q wave trough can serve as a cardiac beat reference time point to determine various cardiac timing signal features. In block 412, one or more morphological events may be extracted from the PPG signal, including the onset and peak of the PPG pulse, from which the first derivative of the PPG pulse (the maximal slope of the upstroke PPG pulse) may be determined. The PPG signal and/or derivative thereof allow determination (e.g., calculation) of PPG-derived signal features and cardiac timing features such as the PAT and/or the PTT by combining other features from the ECG and/or PCG signals. In block 414, morphological events are detected in the PCG signal, including peaks of S1 and S2 sounds in each cardiac cycle that help to determine cardiac timing signal features such as the PEP and left ventricular ejection time (LVET). Further details about the calculation of cardiac timing signal features and PPG signal features are given below.

The time series of morphological events and calculated signal features may be input to the block 416, where potential artifacts including presence of arrhythmia, motion, anomalies, and outliers may be detected and rejected from the time series of signal features. The signal features that are now substantially free from potential artifacts are fed to the block 418, where the time series of signal features are averaged over a desired time window such as 15 s, 30 s, 45 s, 60 s, etc. A feature vector may be created with the averaged signal features including cardiac timing signal features and PPG signal features, and/or other vital sign measurements including but not limited to heart rate, breathing rate, etc. sensed by and/or determined from information obtained by sensor device 100. Patient-specific information such as age, gender, height, weight, and/or body mass index obtained, for example, by entry via an input device or graphical interface, or from stored information, from block 420 are incorporated with the feature vector.

The feature vector comprising the cardiac timing signal features, PPG features, vital signs, and/or patient information may be applied to one or more independent regression models at block 422 to predict SBP, DBP, and MBP values, according to one or more embodiments. For example, one or more of linear regression, polynomial regression, ridge regression, stepwise regression, Lasso regression, and/or ElasticNet regression may be implemented and trained with one or more machine learning techniques including multivariate linear regression, support vector machines, neural networks, and/or random forest.

In block 424, the predicted outputs of SBP, DBP, and MBP values may be displayed or logged continuously according to the rate of the NIBP determination, for example periodically every beat or cardiac cycle, second, minute, and/or hour.

Figure 5:
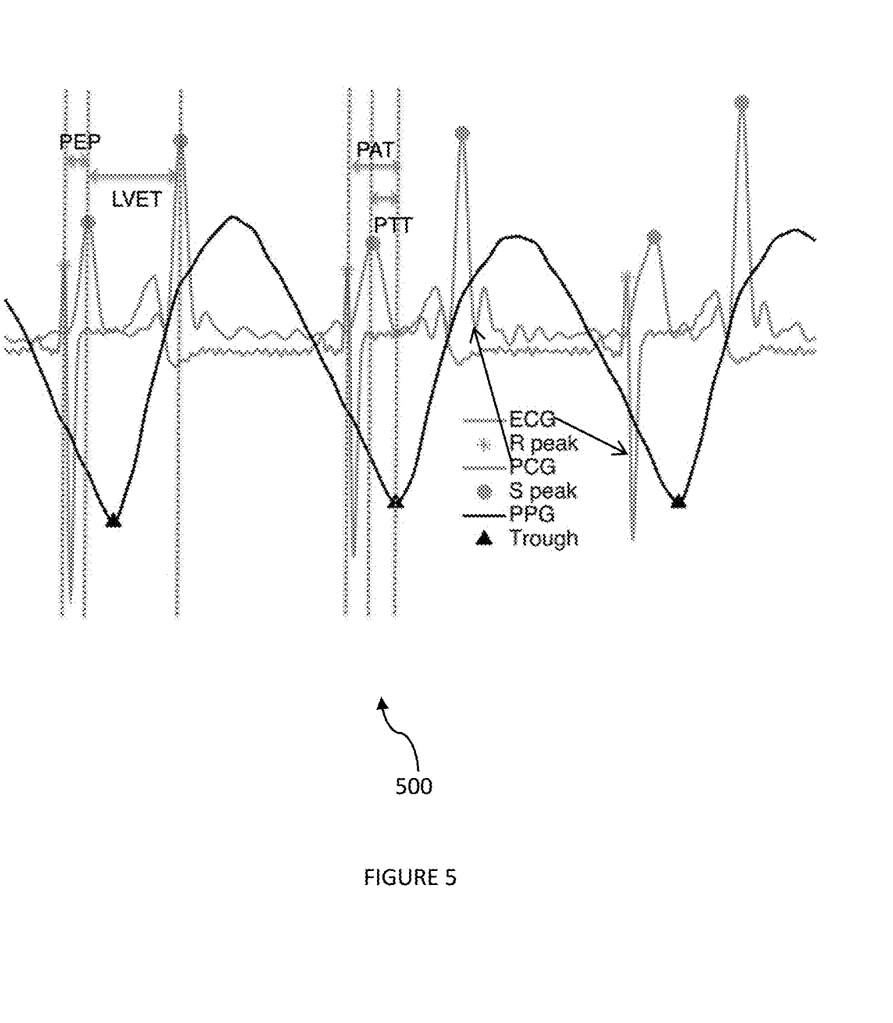
FIG. 5 illustrates a combination of waveforms from which a method may be performed to calculate cardiac timing signal features according to one or more embodiments.

FIG. 5 illustrates a combination of waveforms 500 from which a method may be performed to calculate cardiac timing signal features according to one or more embodiments. In particular, FIG. 5 shows a few cardiac cycles of simultaneously recorded ECG, PPG, and PCG signals using sensor device 100, and the detected morphological events such as R wave peaks of ECG, onset trough of PPG, and peaks of S1 and S2 sounds in PCG. The onset of the PPG pulse may be used to determine the time delays from an R peak of ECG and a peak of S1 sound of PCG. Accordingly, a time delay between the R peak of ECG and the onset of a corresponding PPG pulse may be determined as the PAT of a cardiac cycle. On the other hand, a time delay between the peak of S1 sound of PCG and the onset of a corresponding PPG pulse may be determined as the PTT of a cardiac cycle. In addition to the calculation of PAT and PTT, the PEP may be calculated as a time delay between an R peak of ECG and a peak of S2 sound measured from PCG. Further, LVET may be calculated as a time delay between the peak of S1 sound and the peak of S2 sound in the PCG signal.

Figure 6:
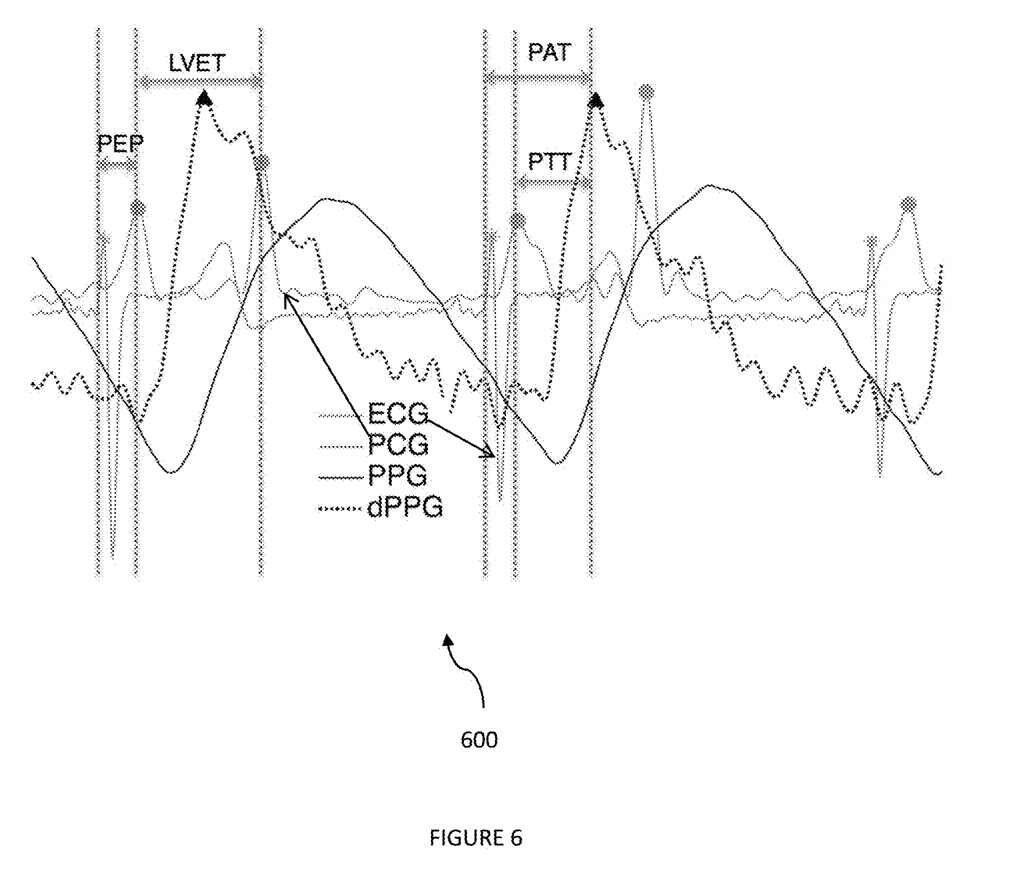
FIG. 6 illustrates another combination of waveforms from which a method may be performed to calculate cardiac timing signal features.

FIG. 6 illustrates another combination of waveforms 600 from which a method may be performed to calculate cardiac timing signal features. In particular, FIG. 6 shows cardiac cycles of simultaneously recorded ECG, first derivative of PPG (dPPG), and PCG signals using an embodiment of sensor device 100, and detected morphological events such as R wave peaks of ECG, peaks of the first derivative of PPG, and peaks of S1 and S2 sounds in PCG. The peak of the first derivative of the PPG pulse may be used to determine a time delay from an R peak of ECG and a peak of S1 sound of PCG. Accordingly, a time delay between the R peak of ECG and a peak of the corresponding first derivative of a PPG pulse may be determined as the PAT of a cardiac cycle. On the other hand, a time delay between a peak of S1 sound of PCG and a peak of the corresponding first derivative of the PPG pulse may be determined as the PTT of a cardiac cycle. In addition to the calculation of PAT and PTT, the PEP (the time interval from the beginning of electrical stimulation of the ventricles to the opening of the aortic valve (electrical systole)) may be calculated as a time delay between an R peak of ECG and a peak of S2 sound measured from PCG. Further, LVET (the time interval from the opening to the closing of the aortic valve (mechanical systole)) may be calculated as a time delay between the peak of S1 sound and the peak of S2 sound in the PCG signal.

Figure 7:
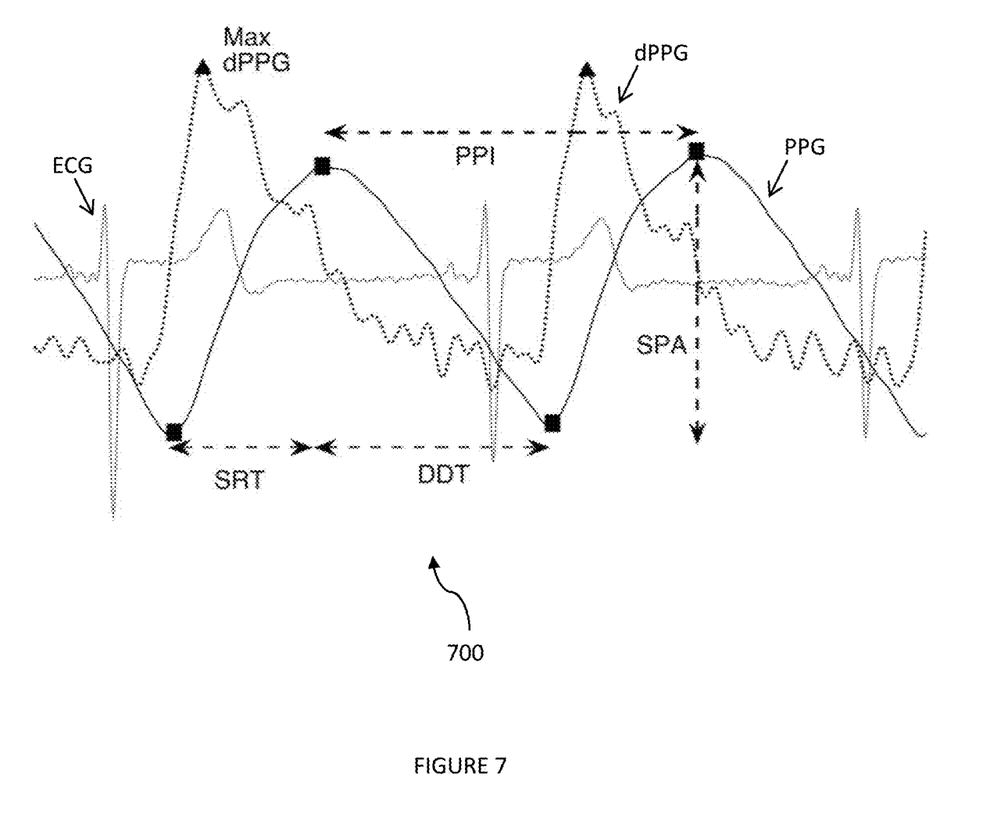
FIG. 7 illustrates an example of a measured PPG signal waveform with its corresponding first derivative waveform dPPG and signal features that may be derived therefrom in accordance with one or more embodiments.

FIG. 7 illustrates at 700 an example of a measured PPG signal waveform with its corresponding first derivative waveform dPPG and signal features that may be derived therefrom in accordance with one or more embodiments. As examples of such derivation, the signal features may be extracted or calculated from the measured PPG signal waveform and/or its corresponding first derivative waveform dPPG. In particular, FIG. 7 illustrates cardiac cycles of simultaneously recorded ECG, dPPG, and PPG signals using sensor device 100, and detected morphological events such as a peak of dPPG and onset troughs and peaks of PPG pulse waves. A simultaneous ECG signal is also shown as a reference for successive cardiac cycles.

One or more of the signal features in FIG. 7 are derived based on the PPG signal and include (i) systolic peak amplitude (SPA) as an amplitude of onset to peak of a PPG pulse, (ii) the systolic rise time (SRT) as the time taken to rise from onset to peak of the PPG pulse, (iii) the diastolic descend time (DDT) as the time taken to descend from the peak to the subsequent onset of a PPG pulse, (iv) the peak-to-peak interval (PPI) as the time interval between two successive peaks of PPG pulse waveforms, (v) the maximal rate of change in upstroke phase of PPG pulse (Max-dPPG) as the peak of the first derivative of the PPG pulse in a cardiac cycle, (vi) the pulse slope as the ratio of SPA to SRT of a PPG pulse, (vii) the systolic pulse wave area (SPWA) as the signal area of upstroke systolic phase from onset to peak of a PPG pulse, (viii) the diastolic pulse wave area (DPWA) as the signal area of descending diastolic phase from peak to onset of the subsequent PPG pulse, and/or (ix) the core perfusion intensity (CPI) as the ratio of SPA to the average intensity determined over a time duration of PPG signal recorded on a central body location such as the chest.

Figure 8:
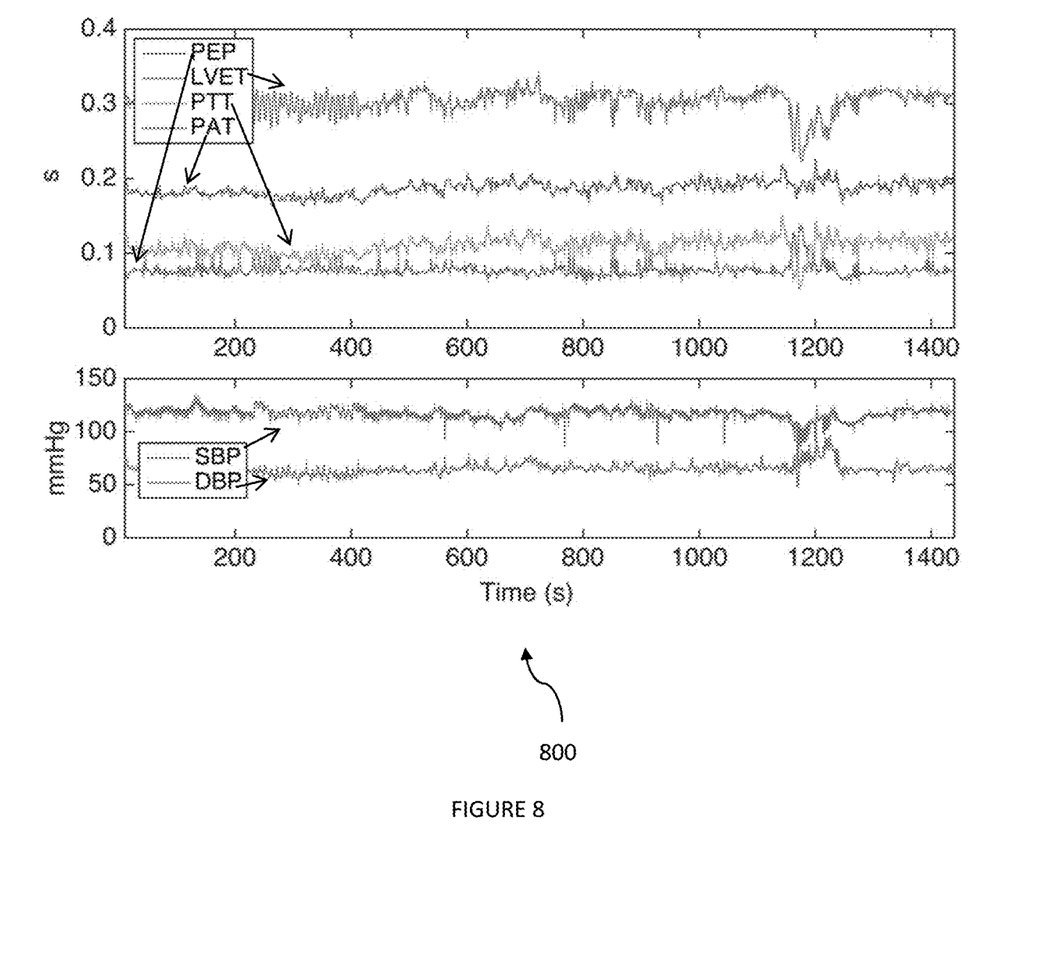
FIG. 8 illustrates an example of cardiac timing signal features derived from cardiac signals, including PEP, LVET, PTT, and PAT detected in a subject according to the algorithm of FIG. 4 and reference measurements of SBP and DBP, in accordance with one or more embodiments.

FIG. 8 illustrates an example of cardiac timing signal features derived from cardiac signals 800, including PEP, LVET, PTT, and PAT detected in a subject according to the algorithm of FIG. 4, in accordance with one or more embodiments. As shown in FIG. 8, cardiac timing signal features such as PEP, LVET, PTT, and PAT may be extracted from simultaneous ECG, PPG, and PCG signals received, e.g., from sensor blocks 404, 406, and 408, respectively. The signal features derived in block 418 of method 400 including cardiac timings features may be valuable physiological signals that can be output as machine-readable outputs for other clinical monitoring and patient health-related applications. The bottom panel of FIG. 8 illustrates reference measurements of SBP and DBP. The significant changes or perturbations in the BP values in the bottom panel show good correspondence to that of measured cardiac timings in the top panel.

Figure 9:
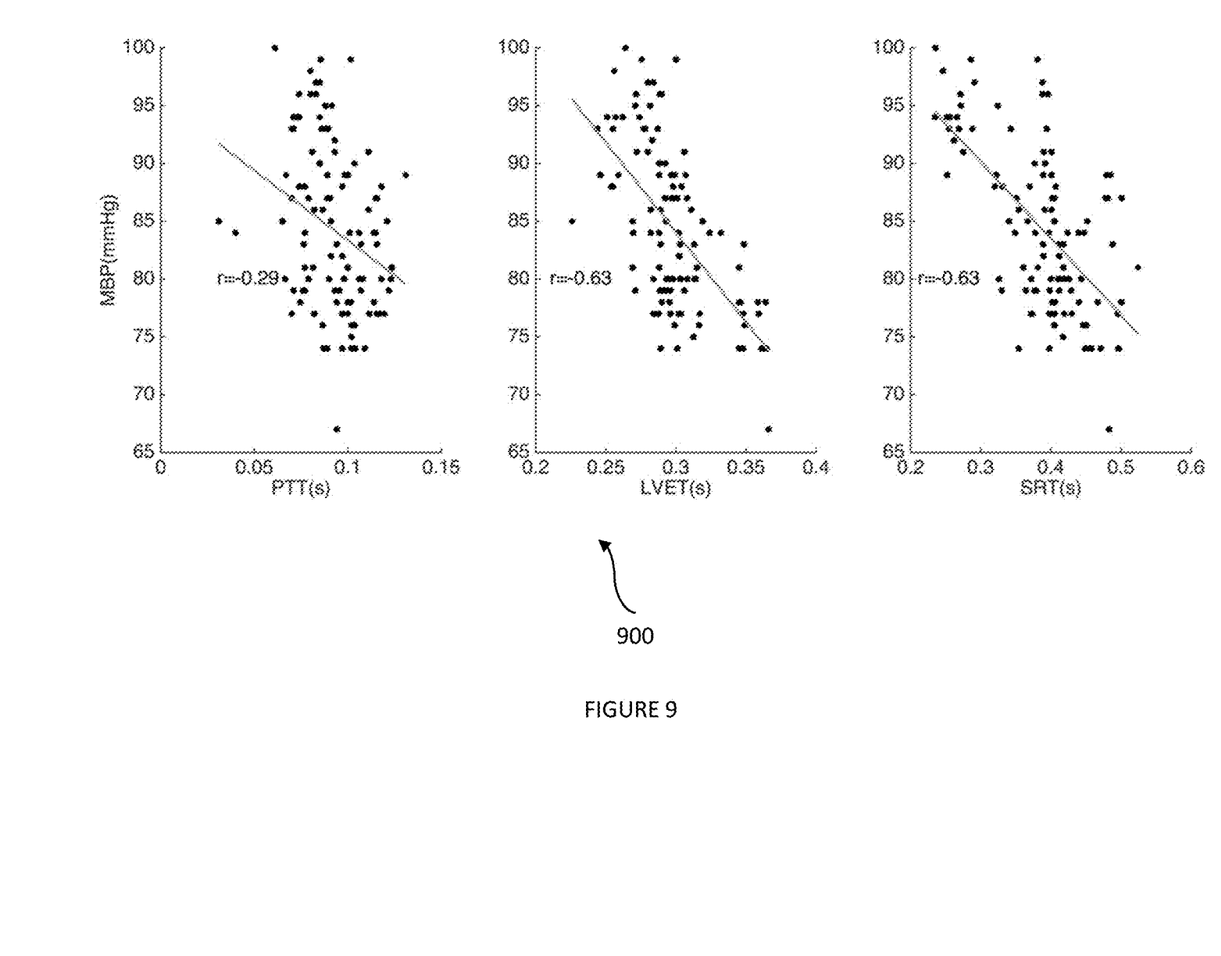
FIG. 9 illustrates an example of correlations of individual signal features for the prediction of NIBP, quantified in a group of individuals performing a sequence of physiological maneuvers inducing changes in BP, according to one or more embodiments.

FIG. 9 illustrates an example of correlations 900 of individual signal features for the prediction of NIBP, quantified in a group of individuals performing a sequence of physiological maneuvers inducing changes in BP, according to one or more embodiments. More particularly, FIG. 9 illustrates graphically linear relationships in PTT, LVET, and SRT compared to a reference MBP measured using a standard automated oscillometry device. In the illustrated example, the PTT feature (left panel) appears to show a relatively low correlation to the reference MBP as compared with the respective correlations of LVET and SRT to MBP. The correlation of PTT derived from peripheral locations such as the finger may correlate relatively stronger to BP in some individuals. However, the PTT derived from a core body location such as the chest may be of relatively less value to predict NIBP, as suggested by the left panel of FIG. 9.

On the other hand, the LVET and SRT plotted in the middle and right panels show a relatively strong correlation to the reference MBP by comparison to the PTT. Thus, even if one considers the predictive power of these signal features individually to be limited as a univariate prediction solution, the fusion of these signal features obtained from ECG, PPG, and PCG sensor modalities as a multivariate solution may offer a relatively more accurate prediction of NIBP with human-readable outputs such as SBP, DBP, and MBP.

Figure 10:
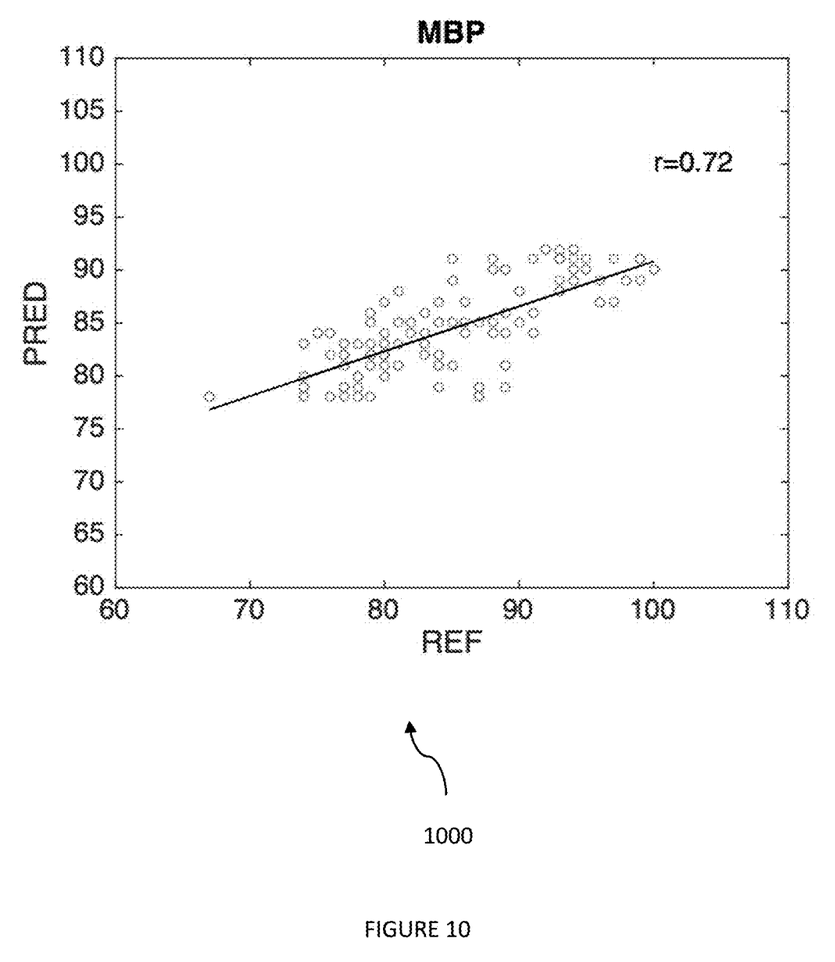
FIG. 10 illustrates a scatter plot of predicted mean blood pressure (MBP) values using multivariate regression (in Y axis) versus reference MBP values measured using a standard automated oscillometry device (in X axis) in a group of individuals performing a sequence of physiological maneuvers inducing changes in BP, according to one or more embodiments.

FIG. 10 illustrates a scatter plot 1000 of predicted MBP values (in Y axis) using multivariate regression as in method 400, versus reference MBP values (in X axis) measured using a standard automated oscillometry device in a group of individuals performing a sequence of physiological maneuvers inducing changes in BP, according to one or more embodiments. The predicted MBP values using this embodiment of method 400 shows substantial correlation to that of reference MBP values from automated oscillometry to suggest that NIBP prediction using a sensor device approach according to one or more embodiments described in the present disclosure may provide useful and accurate measurements and/or monitoring of NIBP including SBP, DBP, MBP, and pulse pressure (PP).

Traditional approaches for NIBP measurement, including volume-clamp methods or peripheral pulse transit time methods, require periodic calibration, generally using an upper arm oscillometry device. The calibration procedure using an upper-arm BP cuff allows to transform the measured univariate signal feature in the given individual such as pulse transit time or finger cuff pressure in case of a volume-clamp method into an absolute magnitude of blood pressure, according to a prediction model. Thus, the calibration procedure allows to transform the indirect univariate signal feature into direct absolute magnitude of BP for the given individual. The calibration procedures in these traditional methods may be required intermittently or hourly or daily, for example. Without the calibration routines, these methods can be highly erroneous in their absolute magnitude values of BP.

On the other hand, one or more embodiments described herein need not be limited by a pneumatic cuff for measurement, nor an onerous calibration routine. The BP prediction models or transformation of multivariate signal features including various cardiac timing intervals, signal magnitudes and subject-specific information into absolute magnitudes of BP is obtained by machine-learning in large group individuals with wide range of demographics and disease conditions. With the trained one or more prediction models, the magnitude of NIBP may be mapped according to the various signal features and subject-specific information related to the given individual (e.g., patient) without requiring a calibration procedure using an upper arm cuff and input that calibration value in to the system. In one or more embodiments, calibration using an upper arm oscillometry device may be performed in combination to predict the NIBP magnitude more accurately.

The wearable sensor device described in this disclosure may include a wearable patch sensor in a fully disposable or semi-disposable form according to one or more embodiments, and/or a reusable electronic device in one or more embodiments. This wearable sensor device may be connected/paired wirelessly to one or more external devices, including but not limited to a smartphone, tablet, or relay. In one or more embodiments, the machine-readable signal features may include cardiac timing signal features and/or PPG signal features may all be processed using the sensor processor, application, and memory and produce the human- and/or machine-readable outputs such as NIBP or other vital sign values, including but not limited to the signal features described herein, then encrypted and transmitted via a BLE link to an external relay for further analysis, storage, and/or viewing. In one or more embodiments, the sensor signals or signal features may be processed in a processor and memory, then encrypted and transmitted via a BLE link to an external relay and/or cloud, where processing of those signals or features may be carried out to determine NIBP values and/or other information. The predicted NIBP values may be displayed on the sensor, on a smartphone application screen, on a computer screen, or on any other suitable device. From a smartphone or cloud server, for example, an analysis report with trends of continuous NIBP and other vital sign values can be produced and sent to the user/subject, physician, family member, or elsewhere as directed.

A method and system for determining NIBP has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

The method and system disclosed may take any of numerous forms. For example, the predicted NIBP may be provided via output 424 as a numeric measure of NIBP or a continuous graphical waveform, provided wirelessly or otherwise. In some embodiments, output 424 may be non-numeric and provide, for example, an alarm if the measured, predicted, or estimated NIBP exceeds a threshold, or indicate a general status, for example that the NIBP is in an "acceptable range" or outside the acceptable range. The non-numeric indicator may be a visible or audible indicator (e.g., alarm), or a wireless signal. The result may be wirelessly transmitted for any of further data extraction, human or machine analysis, storage (local, remote, or cloud-based), or monitoring. More than one of these outputs or further use of the outputs are also contemplated. In addition, or alternatively, any or all of the outputted information may be provided via the display or in another fashion that one of ordinary skill in the art would readily understand.

In one or more embodiments, one or more of the algorithm functions may be performed externally of sensor device 100. In such embodiments, an intermediate stage of the algorithm may include outputting current data, information, or analysis. For example, the extracted timing waveforms may be transmitted wirelessly for further processing and/or analysis to determine or predict the NIBP. In one or more embodiments, the analysis results may be returned to sensor device 100 for further processing, data extraction, human or machine analysis, storage, or monitoring.

Although one or more embodiments are disclosed in which sensor device 100 may provide information wirelessly, sensor device 100 may include, additionally or alternatively, structure capable of transmitting information via wires. For example, sensor device 100 may have one or more ports to connect wires via which information may be transmitted. Further, although a single sensor device 100 is described by way of example, one or more of the disclosed functions may be performed by one or more other sensor devices, whether wearable or unworn, and/or devices located externally of the subject.

As indicated above, the foregoing description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

What is claimed is:

1. A sensor device, comprising:
one or more sensors configured to:
sense physiological changes associated with cardiovascular function and provide outputs corresponding to the sensed physiological changes, and
detect an electrocardiograph (ECG) signal, a photoplethysmograph (PPG) signal, and a phonocardiograph (PCG) signal of a patient from the outputs provided by the one or more sensors; and
a memory storing a program, in response to execution, causes a processor to perform operations comprising:
filtering the detected ECG, PPG, and PCG signals by detecting and rejecting artifacts from the detected ECG, PPG, and PCG signals, the artifacts including at least one presence of: arrhythmia, motion, anomalies, and outliers to produce filtered ECG, PPG, and PCG signals;

extracting multivariate signal features including magnitudes and cardiac timing intervals from the filtered ECG, PPG, and PCG signals;

averaging time series of the multivariate signal features over a predetermined time window;

processing the averaged multivariate signal features and subject-specific information using an application including an independent Blood Pressure (BP) prediction model to determine Noninvasive Blood Pressure (NIBP) including systolic blood pressure (SBP), diastolic blood pressure (DBP), and mean blood pressure (MBP) values, wherein the independent BP prediction model is derived by machine-learning in large group individuals including demographics and disease conditions, wherein with the independent BP prediction model, the SBP, DBP, and MBP values of the NIBP are mapped according to the averaged multivariate signal features and the subject-specific information; and displaying or continuously logging the SBP, DBP, and MBP values.

2. The sensor device of claim 1, wherein the processor performs further operations comprising:

displaying or continuously logging pulse pressure; wherein the displaying or continuously logging is at a rate including beat, second, minute, and/or hour.

3. The sensor device of claim 1, wherein the processor performs further operations comprising displaying or continuously logging an indication of the NIBP exceeding a threshold.

4. The sensor device of claim 1, wherein the processor performs further operations comprising: outputting the multivariate signal features formatted for one or more of machine or human readability;

wherein the outputted multivariate signal features include the multivariate signal features derived from the detected ECG, PPG and/or PCG signals, including one or more of cardiac timing intervals or core perfusion intensity; and wherein the outputted multivariate signal features are one or more of predictors or correlates of the NIBP.

5. The sensor device of claim 1, wherein the determined NIBP measurement is calibration-free.

6. The sensor device of claim 1, wherein the processor performs further operations comprising displaying or continuously logging an indicator of blood pressure other than a numeric blood pressure value.

7. The sensor device of claim 1, further comprising a base configured to physically support the one or more sensors adapted to be worn by a subject of the sensed physiological changes associated with cardiovascular function.

8. The sensor device of claim 6, wherein the indicator is a non-numeric output.

9. A method to determine noninvasive blood pressure, comprising:

sensing, by a sensor, physiological changes associated with cardiovascular function;

detecting, by the sensor, electrocardiograph (ECG), photoplethysmograph (PPG), and phonocardiograph (PCG) signals based on the sensed physiological changes;

filtering, by a processor, the detected ECG, PPG, and PCG signals by detecting and rejecting artifacts from the detected ECG, PPG, and PCG signals, the artifacts including at least one presence of: arrhythmia, motion, anomalies, and outliers to produce filtered ECG, PPG, and PCG signals;

extracting, by the processor, multivariate signal features including magnitudes and cardiac timing intervals from the filtered ECG, PPG, and PCG signals;

averaging time series of the multivariate signal features over a predetermined time window;

processing, by the processor, the averaged multivariate signal features and subject-specific information using an application including an independent Blood Pressure (BP) prediction model to determine Noninvasive Blood Pressure (NIBP) including systolic blood pressure (SBP), diastolic blood pressure (DBP), and mean blood pressure (MBP) values, wherein the independent BP prediction model is derived by machine-learning in large group individuals including demographics and disease conditions, wherein with the independent BP prediction model, the SBP, DBP, and MBP values of the NIBP are mapped according to the averaged multivariate signal features and the subject-specific information; and displaying or continuously logging the SBP, DBP, and MBP values.

10. The method of claim 9, further comprising:

displaying or continuously logging pulse pressure; and wherein the displaying or continuously logging is at a rate including beat, second, minute, and/or hour.

11. The method of claim 9, further comprising displaying or continuously logging an indication of the NIBP exceeding a threshold.

12. The method of claim 9, further comprising:

outputting, by the processor, the multivariate signal features formatted for one or more of machine or human readability;

wherein the outputted multivariate signal features include the multivariate signal features derived from the detected ECG, PPG and/or PCG signals, including one or more of cardiac timing intervals or core perfusion intensity; and wherein the outputted multivariate signal features are one or more of predictors or correlates of the NIBP.

13. The method of claim 12, wherein the determined NIBP measurement is calibration-free.

14. The method of claim 9, further comprising displaying or continuously logging an indicator of the blood pressure condition other than a numeric blood pressure value.

15. The method of claim 14, wherein the indicator is a non-numeric output.

16. The method of claim 9, further comprising:

attaching, to a subject of the sensing, a base configured to physically support the sensor;

wherein the sensor performs the sensing of the physiological changes associated with cardiovascular function of the subject.

17. A system to predict Noninvasive Blood Pressure (NIBP), comprising:

a sensor device including:

one or more sensors configured to:

sense physiological changes associated with cardiovascular function and provide outputs corresponding to the sensed physiological changes, and detect an electrocardiograph (ECG) signal, a photoplethysmograph (PPG) signal, and a phonocardiograph (PCG) signal from the outputs provided by the one or more sensors;
a processor configured to:
  filter the detected ECG, PPG, and PCG signals by detecting and rejecting artifacts from the detected ECG, PPG, and PCG signals, the artifacts including at least one presence of: arrhythmia, motion, anomalies, and outliers to produce filtered ECG, PPG, and PCG signals;
  extract multivariate signal features including magnitudes and cardiac timing intervals from the filtered ECG signal, PPG signal, and PCG signal;
  average time series of the multivariate signal features over a predetermined time window; and
a wireless transmitter configured to transmit wirelessly the multivariate signal features to a computer; and
the computer configured to:
  process the averaged multivariate signal features and subject-specific information using an application including an independent Blood Pressure (BP) prediction model to determine Noninvasive Blood Pressure (NIBP) including systolic blood pressure (SBP), diastolic blood pressure (DBP), and mean blood pressure (MBP) values, wherein the independent BP prediction model is derived by machine-learning in large group individuals including demographics and disease conditions,
  wherein with the independent BP prediction model, the SBP, DBP, and MBP values of the NIBP are mapped according to the averaged multivariate signal features and the subject-specific information; and
  display or continuously log the SBP, DBP, and MBP values.

18. The system of claim 17, wherein the computer is further configured to display or continuously log an indication of the NIBP exceeding a threshold.

19. The system of claim 17,
wherein the computer is further configured to output the multivariate signal features formatted for one or more of machine or human readability;
wherein the outputted multivariate signal features include the multivariate signal features derived from the detected ECG, PPG and/or PCG signals, including one or more of cardiac timing intervals or core perfusion intensity; and
wherein the outputted multivariate signal features are one or more of predictors or correlates of the NIBP.

20. The system of claim 19,
wherein the determined NIBP measurement is calibration-free.

* * * * *